United States Patent [19]
Sivik et al.

[11] Patent Number: 6,100,233
[45] Date of Patent: Aug. 8, 2000

[54] ODOR CONTROL COMPOSITIONS COMPRISING β-KETOESTER PRO-FRAGRANCES

[75] Inventors: Mark Robert Sivik, Fairfield; John Cort Severns, West Chester; Frederick Anthony Hartman, Cincinnati; Toan Trinh, Maineville, all of Ohio

[73] Assignee: The Procter & Gamble Company, Cincinnati, Ohio

[21] Appl. No.: 09/242,652

[22] PCT Filed: Aug. 19, 1997

[86] PCT No.: PCT/US97/14614

§ 371 Date: Mar. 18, 1999

§ 102(e) Date: Mar. 18, 1999

[87] PCT Pub. No.: WO98/07455

PCT Pub. Date: Feb. 26, 1998

Related U.S. Application Data

[60] Provisional application No. 60/024,117, Aug. 19, 1996.

[51] Int. Cl.$^7$ .............................. A61K 7/46; A61L 9/04; A61L 9/00; A61L 9/015; C11D 3/50
[52] U.S. Cl. ................................. 512/26; 512/2; 512/25; 512/27; 424/76.4; 424/76.2; 424/76.1; 510/131; 510/107
[58] Field of Search .................................. 512/2, 25, 26, 512/27; 424/76.4, 76.2, 76.1; 510/131, 107

[56] References Cited

U.S. PATENT DOCUMENTS

| | | | |
|---|---|---|---|
| 3,074,892 | 1/1963 | Kulka | 252/305 |
| 3,779,932 | 12/1973 | Jaggers et al. | 252/108 |
| 3,830,930 | 8/1974 | Moeller et al. | 424/308 |
| 3,849,326 | 11/1974 | Jaggers et al. | 252/89 |
| 3,870,759 | 3/1975 | Inamoto et al. | 260/586 |
| 4,524,018 | 6/1985 | Yemoto et al. | 252/522 |
| 4,994,266 | 2/1991 | Wells | 424/76.7 |
| 5,081,111 | 1/1992 | Akimoto et al. | 525/285 |
| 5,232,612 | 8/1993 | Trinh et al. | 252/8.6 |
| 5,266,592 | 11/1993 | Grub et al. | 514/452 |
| 5,378,468 | 1/1995 | Suffis et al. | 424/401 |
| 5,506,201 | 4/1996 | McDermott et al. | 512/4 |
| 5,578,563 | 11/1996 | Trinh et al. | 510/513 |
| 5,626,852 | 5/1997 | Suffis et al. | 424/401 |
| 5,663,134 | 9/1997 | Trinh et al. | 510/406 |
| 5,670,475 | 9/1997 | Trinh et al. | 510/470 |
| 5,739,100 | 4/1998 | Horino et al. | 512/25 |
| 5,783,544 | 7/1998 | Trinh et al. | 510/293 |
| 5,858,335 | 1/1999 | Lucas et al. | 424/65 |
| 5,861,145 | 1/1999 | Lucas et al. | 424/65 |
| 5,861,147 | 1/1999 | Dodd et al. | 424/65 |
| 5,871,718 | 2/1999 | Lucas et al. | 424/65 |
| 5,871,719 | 2/1999 | Lucas et al. | 424/65 |
| 5,874,070 | 2/1999 | Trinh et al. | 424/65 |
| 5,897,854 | 4/1999 | Lucas et al. | 424/65 |
| 5,905,067 | 5/1999 | Chapman et al. | 510/368 |
| 5,928,631 | 7/1999 | Lucas et al. | 424/65 |
| 5,939,060 | 8/1999 | Trinh et al. | 424/76.4 |
| 5,942,214 | 8/1999 | Lucas et al. | 424/65 |

FOREIGN PATENT DOCUMENTS

| | | | |
|---|---|---|---|
| 0786 247 A1 | 7/1997 | European Pat. Off. | A61K 7/46 |
| 1923223 | 5/1969 | Germany . | |
| 2509967 | 3/1975 | Germany | C07C 69/02 |
| 5-230496 | 9/1993 | Japan | A61K 7/46 |
| 7-179328 | 7/1995 | Japan . | |
| WO 94/06441 | 3/1994 | WIPO | A61K 31/74 |
| WO 95/04809 | 2/1995 | WIPO | C11D 3/50 |
| WO 96/05358 | 2/1996 | WIPO | D06M 15/11 |

OTHER PUBLICATIONS

P.M. Muller, D. Lamparsky *Perfumes Art, Science, & Technology* Blackie Academic & Professional (New York, 1994) "Perfumery Applications: Functional Products," J. K. Funesti.

Chem. Abstracts #69416, vol. 117, No. 7, Aug. 7, 1992.
Chem. Abstracts #278389, vol. 119, No. 26, Dec. 27, 1993.

*Primary Examiner*—Gabrielle Brouillette
*Assistant Examiner*—Monique T. Cole
*Attorney, Agent, or Firm*—Richard S. Echler, Sr.; Kim W. Zerby; Jacobus C. Rasser

[57] ABSTRACT

The present invention relates to a fragrance delivery system which comprises one or more β-ketoester pro-fragrances or pro-accords, said fragrance delivery system useful in a stable, preferably clear, aqueous odor-absorbing composition. The odor-absorbing composition can be further characterized in that they comprise soliblized, uncomplexed cyclodextrin, and cyclodextrin compatible antimicrobial actives, cyclodextrin compatible surfactants, cyclodextrin compatible humectants, or mixtures thereof. The aqueous odor-absorbing composition are for use on inanimate surfaces, especially fabrics, and more specifically, clothes, in order to restore and/or maintain freshness by reducing malodor without the need for washing or dry cleaning.

9 Claims, No Drawings

ODOR CONTROL COMPOSITIONS COMPRISING β-KETOESTER PRO-FRAGRANCES

This application is a 371 of PCT/US97/14614, filed Aug. 19, 1997.

This application claims priority under Title 35, United States Code 119(e) from Provisional Application Ser. No. 60/024,117, filed Aug. 19, 1996.

FIELD OF THE INVENTION

The present invention relates to a fragrance delivery system which comprises one or more β-ketoester pro-fragrances or pro-accords, said fragrance delivery system useful in a stable, preferably clear, aqueous odor-absorbing compositions. The odor-absorbing compositions can be further characterized in that they comprise solubilized, uncomplexed cyclodextrin, and cyclodextrin compatible antimicrobial actives, cyclodextrin compatible surfactants, cyclodextrin compatible humectants, or mixtures thereof. The odor-absorbing compositions of the present invention are designed to control odors caused by a broad spectrum of organic odoriferous materials. Preferably, the aqueous odor-absorbing compositions are for use on inanimate surfaces, especially fabrics, and more specifically, clothes, in order to restore and/or maintain freshness by reducing malodor without the need for washing or dry cleaning.

BACKGROUND OF THE INVENTION

Cultural and aesthetic standards have influenced the permissible level of human and environmental malodors and control of these odors has been the focus of investigation for many centuries. In general, these investigations have been focused on either of two approaches, namely: (a) odor masking, in which a substance of strong yet relatively pleasant odor is introduced into the proximity of a less pleasant odor source with the intent of overburdening the olfactory receptors with the dominant pleasant odor, or (b) sequestering the undesired odorous substance in a non-volatile form either by chemical reaction, adsorption or absorption on a sorbent material exhibiting a preference for the odorous substance.

In general, articles made of fabric absorb odors and this fact has a pejorative consequence as it relates to the perceived cleanliness of said articles. For example, it has long been recognized that items which are comprised of fabric, especially articles of clothing, can be clean in the sense that the article is free of dirt (i.e. has not been worn since it was laundered), yet this article is rendered "dirty" due to exposure of the article to certain malodors inter alia cigarette and cigar smoke, or fried food odors. This exposure can often occur when the item of apparel is simply hanging in a closet. Although it is frustrating when articles of "common apparel" require re-laundering due to malodor absorption, the consumer is faced with both inconvenience and added expense when certain items are prematurely rendered unfit for wear, for example, items comprised of natural fur or items requiring "dry-cleaning". Indeed, articles such as rugs, carpeting and draperies which are not easily removable nor easily cleaned, present a particular problem when exposed to persistent malodor sources.

Odor masking, although effective in the short term, has certain limitations. First, masking does not remove or eliminate the source of the malodor. Secondly, when scents and perfumes are used to overcome malodors, the user must make sure an effective and constant level of masking agent is present to avoid too low a level of masking agent that may not be sufficient to cover-up the malodor. In turn, too high a level of masking agent may itself produce an undesirable effect. The premature depletion of the masking agent can be an additional concern.

Sequestration has thus become the method of choice for elimination and control of both human and environmental malodors. The more effective approach has been to sequester the undesired malodor primarily by adsorption. Attempts have previously been made to re-freshen clothing, rugs, draperies, and the like, by applying malodor absorbic materials. Many of these processes have been successful, yet the fabric which has been deodorized is typically left without the desired "fresh" or "clean" scent desirable to the consumer.

Accordingly, there remains a need in the art for a malodor control composition which absorbs malodors thereby removing unwanted smells and at the same time releasing desirable fragrances which provide an aesthetically pleasing environment. There is especially a need for odor absorbing compositions which have the capacity to release enduring fragrances which are not themselves absorbed by the malodor absorbing agent.

BACKGROUND ART

The following relate to the subject matter of fragrance ingredients. U.S. Pat. No. 5,626,852 Suffis et al., issued May 6, 1997; U.S. Pat. No. 5,232,612 Trinh et al., issued Aug. 3, 1996; U.S. Pat. No. 5,506,201 McDermott et al., issued Apr. 9, 1996; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky *Perfumes Art, Science, & Technology* Blackie Academic & Professional, (New York, 1994) is included herein by reference.

SUMMARY OF THE INVENTION

The present invention relates to the aforementioned needs in that it has been surprisingly discovered that a mixture of malodor absorbing components and a fragrance delivery system can be applied to fabric wherein the malodor is eliminated and a lasting scent or fragrance is provided to the de-odorized fabric. The fragrance delivery system of the present invention is comprised of one or more pro-fragrances or pro-accords which are capable of releasing one or more fragrance raw materials.

The pro-fragrances and pro-accords described herein comprise fragrance raw material alcohols in a stable, releasable β-ketoester form. The pro-fragrance containing malodor control compositions of the present invention can comprise any number of pro-fragrances which when taken together are capable of releasing complex perfume fragrances. However, the β-ketoesters of the present invention which are pro-accords are capable of undergoing chemical transformation and thereby releasing one or more fragrance raw materials in addition to the fragrance raw material alcohol used to prepare the original parent pro-accord. In addition, the pro-fragrances and pro-accords of the present invention are suitable for delivery of any type of fragrance "characteristic" desired by the formulator.

The first aspect of the present invention relates to malodor control compositions which provide fabric with enhanced fragrance longevity, comprising:
 a) at least about 0.01%, preferably from about 0.01% to about 15%, more preferably from about 1% to about 5%, most preferably from about 0.1% to about 1% by weight, of a β-ketoester having the formula:

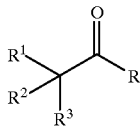

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

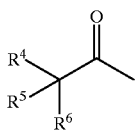

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;
 b) optionally from about 0.01% to about 5%, preferably from about 0.5% to about 2% by weight, of uncomplexed cyclodextrin, said cyclodextrin is selected from the group consisting of highly water soluble cyclodextrins, highly water soluble cyclodextrin derivatives, and mixtures thereof, preferably α-cyclodextrin, hydroxypropyl α-cyclodextrin, hydroxypropyl β-cyclodextrin, methylated α-cyclodextrin, methylated β-cyclodextrin, and mixtures thereof,
 c) optionally from about 0.05% to about 0.3% by weight, of a cyclodextrin compatible surfactant, said surfactant selected from the group consisting of block copolymers of ethylene oxide and propylene oxide, polyalkyleneoxide polysiloxanes, alkyldiphenyl oxide disulfonate anionic surfactants having the formula:

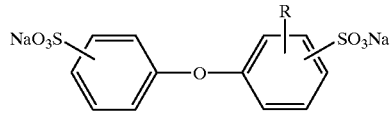

wherein R is $C_{12}$–$C_{22}$ linear or branched alkyl, and mixtures thereof; and
 d) carriers and adjunct ingredients.

The present invention further relates to malodor control compositions which further comprise:
 e) optionally, an effective amount, to kill, or reduce the growth of microbes, of cyclodextrin compatible and water soluble antimicrobial active, preferably from about 0.001% to about 0.2% by weight, and preferably selected from the group consisting of halogenated compounds, cyclic nitrogen compounds, quaternary compounds, and phenolic compounds;
 f) optionally, but preferably, an effective amount to improve acceptance of the composition, typically from about 0.003% to about 0.5%, preferably from about 0.01% to about 0.3% by weight, of hydrophilic perfume;
 g) optionally, but preferably, from about 0.01% to about 3%, more preferably from about 0.05% to about 1% by weight; of low molecular weight polyol;
 h) optionally, from about 0.001% to about 0.3%, preferably from about 0.01% to about 0.1% by weight; of aminocarboxylate chelator;
 i) optionally, but preferably, an effective amount of metallic salt, preferably from about 0.1% to about 10%, more preferably from about 0.2% to about 5% by weight; especially water soluble copper and/or zinc salts, for improved odor benefit; and
 j) optionally, an effective amount of solubilized, water-soluble, antimicrobial preservative, preferably from about 0.0001% to about 0.5%, more preferably from about 0.0002% to about 0.2% by weight.

The present invention further relates to malodor control compositons which further comprise one or more adjunct ingredients, said adjunct ingredient is selected from the group consisting of:
 i) from 0% to about 3% by weight, of a low molecular weight polyol;
 ii) from 0% to about 0.3% by weight, of an aminocarboxylate chelator;
 iii) from 0% to about 5% by weight, of a copper salt, a zinc salt, or mixtures thereof;
 iv) from 0% to about 0.5% by weight, of a perfume;
 v) from 0% to about 0.5% by weight, of a solubilized, water-soluble, antimicrobial preservative; and
 vi) mixtures thereof.

The present invention also relates to concentrated compositions, wherein the level of cyclodextrin is from about 3% to about 20%, more preferably from about 5% to about 10%, by weight of the composition which are diluted to form compositions with the usage concentrations of cyclodextrin of, e.g., from about 0.1% to about 5%, by weight of the diluted composition, as given hereinabove, which are to the "usage conditions".

The present invention also comprises the use of small particle diameter droplets of the compositions herein, even those which do not contain a cyclodextrin or an antimicrobial, to treat surfaces, especially fabrics, to provide superior performance, e.g., the method of applying the compositions to fabrics, etc. as very small particles (droplets) preferably having average particle sizes (diameters) of from about 10 µm to about 120 µm, more preferably from about 20 µm to about 100 µm.

In another aspect of the invention herein, compositions that contain combinations of water soluble antimicrobial actives, especially those described hereinafter, and especially the bis-beguanide alkane compounds described hereinafter, and the surfactants described hereinafter, especially the polyalkyleneoxide polysiloxanes described hereinafter provide superior antimicrobial action in aqueous solutions, either by themselves, or in combination with the other ingredients, including the cyclodextrin. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (0° C.) unless otherwise specified. All documents cited are in relevant part, incorporated herein by reference.

DETAILED DESCRIPTION OF THE INVENTION

The present invention relates to stable, preferably clear, aqueous odor absorbing compositions comprising a fragrance delivery system which is capable of releasing fragrance raw materials over a protracted period of time. In addition, the fragrance delivery system comprises pro-fragrances and pro-accords which are not complexed by the cyclodextrins of the present invention.

Fragrance Delivery System

The malodor control compositions of the present invention comprise a fragrance delivery system which lays down one or more "pro-fragrance" compounds onto the fabric surface during the laundry wash cycle which are capable of releasing a fragrance raw material alcohol or in the case of "pro-accords" the compounds are capable of releasing a mixture of fragrance raw materials. The key advantages provided by the β-ketoester pro-fragrances or pro-accords of the present invention include chemical stability in the final product matrix, ease of formulation into the product matrix, and a highly desirable rate of fragrance raw material alcohol release.

The β-ketoester pro-fragrances and pro-accords of the present invention begin delivering the fragrance raw materials to the fabric surface once the fabric is exposed to the maolodor control agent. For the purposes of the present invention the term "pro-fragrance" is defined as "a β-ketoester which releases a fragrance raw material alcohol" whereas a "pro-accord" is defined as "β-ketoester which release two or more fragrance raw materials". For the purposes of the present invention, however, since a material that is a "pro-fragrance" in one embodiment can serve as a "pro-accord" in a different embodiment, the term "pro-fragrance" is used interchangeably with the term "pro-accord" and either term may be used to stand equally well for either β-ketoester pro-fragrance molecules, β-ketoester pro-accord molecules, or both collectively. These "pro-fragrance" compounds are rapidly deposited onto the fabric surface due to the high fabric substantivity of the compounds and once deposited, begin to release the fragrance raw material alcohols during the wash and drying cycles. Because the β-ketoester "pro-fragrances" of the present invention generally have a higher molecular weight than uncombined fragrance raw material alcohols are therefore less volatile, the "pro-fragrances" of the present invention are a means for effectively delivering fragrance raw materials to the fabric surface even upon exposure to prolonged heating which occurs during automatic dryer usage. Once the laundry cycle is complete, that is the clothing or fabric is dry and ready for use, the "pro-fragrance" continues to release the fragrance raw material alcohol and because this release of material is protracted, the fabric remains "fresh" and "clean" smelling longer.

For the purposes of the present invention "fragrance raw materials" are herein defined as alcohols and ketones having a molecular weight of at least about 100 g/mol and which are useful in imparting an odor, fragrance, essence, or scent either alone or in combination with other "fragrance raw material alcohols and ketones".

Most of the fragrance raw material alcohols which comprise the β-ketoester "pro-fragrances" of the present invention are not deliverable as individual compounds to fabric via the laundry cycle either due to solubility factors (not sufficiently soluble in the liquid laundry liquor), substantivity factors (do not sufficiently adhere to fabric surface), or volatility factors (evaporation during storage). Therefore, the pro-fragrances described herein are a means for delivering certain fragrance raw materials to fabric which could not have previously been effectively or efficiently delivered.

β-Ketoester Pro-fragrances

The compositions according to the present invention comprise one or more β-ketoesters having the formula:

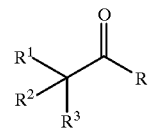

wherein R is alkoxy derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6-dimethyl-1-methylethenylbicyclo[2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-$\Delta^2$-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methylphenyl)ethanol, 1 -phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0$^{(2,6)}$]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4-methyl-1-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1] hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo [3.1.1]heptane, 1,7,7-trimethylbicyclo[2.2.1]heptan-2-ol, 2,6-dimethylheptan-2-ol (dimetol), 2,6,6-trimethylbicyclo [1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol), 3,7-dimethyl-7-methoxyoctan-2-ol (osyrol), 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetrahydrofuran, β-caryophyllene alcohol, vanillin, ethyl vanillin, and mixtures thereof.

More preferably, the fragrance raw material alcohol is selected from the group consisting of cis-3-hexen-1-ol, hawthanol [admixture of 2-(o-methylphenyl)-ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethyl)cyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl-4-isopropenylcyclohexan-3-ol, 4-isopropyl-1-methylcyclohexan-3-ol (menthol), 4-tert-butylcyclohexanol, 2-tert-butyl-4-methylcyclohexanol, 4-isopropylcyclo-hexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy-4-(1-propenyl)phenol, vanillin, and mixtures thereof.

$R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

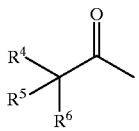

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof.

In one preferred embodiment at least two $R^2$, or $R^3$ units are hydrogen and $R^4$, $R^5$, and $R^6$ units are each hydrogen. In another preferred embodiment two $R^4$, $R^5$, and $R^6$ units are hydrogen and the remaining unit is $C_1$–$C_{20}$ substituted or unsubstituted linear alkyl, $C_3$–$C_{20}$ substituted or unsubstituted branched alkyl, $C_3$–$C_{20}$ substituted or unsubstituted cyclic alkyl; more preferably hexyl, heptyl, octyl, nonanyl, ω-hexenyl, ω-heptenyl, ω-octenyl, ω-nonenyl, and mixtures thereof. Also preferably $R^4$, $R^5$, and $R^6$ are taken together to form a $C_6$–$C_{30}$ substituted or unsubstituted aryl unit, preferably substituted or unsubstituted phenyl and naphthyl. Also preferred embodiments include providing $R^2$ and $R^3$ moieties which provide increased fabric substantivity or which facilitate the rate at which fragrance raw materials are released.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are —CHO; —$CO_2^-M^+$; —$CO_2R^9$; —$CONH_2$; —$CONHR^9$; —$CONR^9{}_2$; wherein $R^9$ is $C_1$–$C_{12}$ linear or branched alkyl); —$SO_3^-M^+$; —$OSO_3^-M^+$; —$N(R^{10})_2$; and —$N^+(R^{10})_3X^-$ wherein each $R^{10}$ is independently hydrogen or $C_1$–$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

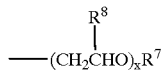

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

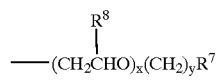

wherein $R^7$ is hydrogen, $C_1$–$C_{18}$ alkyl, $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

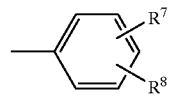

or α and β-naphthyl moieties having the formula:

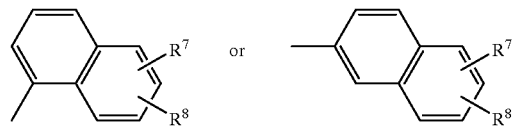

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2^-M^+$; —$CO_2R^9$; —$CONH_2$; —$CONHR^9$; —$CONR^9{}_2$; wherein $R^9$ is $C_1$–$C_{12}$ linear or branched alkyl), —$SO_3^-M^+$, —$OSO_3^-M^+$, —$N(R^{10})_2$, and —$N^+(R^{10})_3X^-$ wherein each $R^{10}$ is independently hydrogen, $C_1$–$C_4$ alkyl, or mixtures thereof; and mixtures thereof, $R^7$ and $R^8$ are preferably hydrogen, $C_1$–$C_6$ alkyl, —$CO_2^-M^+$, —$SO_3^-M^+$, —$OSO_3^-M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

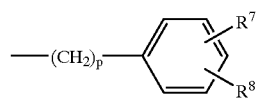

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9{}_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

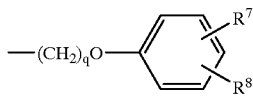

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, q is from 1 to about 14; M is hydrogen or a water soluble cation.

Non-limiting examples of ketones which are releasable by the pro-accords of the fragrance delivery systems of the present invention are α-damascone, β-damascone, δ-damascenone, β-damascenone, muscone, 3,3-dimethylbutanone, methyl phenyl ketone (acetophenone), 4-phenylbutan-2-one (benzyl acetone), 2-acetyl-3,3-dimethyl norborane (camek dh), 6,7-dihydro-1,1,2,3,3-pentamethyl-4(5H) indanone (cashmeran), 4-(1,3)-benzodioxol-5-yl 3-buten-2-one (cassione), 4-(3,4-methylenedioxyphenyl)-2-butanone (dulcinyl), 3-octanone, 6-acetyl-1,2,3,4-tetrahydronaphthalene ketone (florantone t), ethyl-2-n-hexyl acetoacetate (gelsone), 2,6-dimethylundeca-2,6-dien-10-one, 6,10-dimethyl-5,9-undecadien-2-one, 3,3-dimethylcyclohexyl methyl ketone (herbac), 4-(2,6,6-trimethyl-1-cyclohexen-1-yl)-3-buten-2-one (β-ionone), 4-(2,6,6-trimethyl-2-cyclohexen-1-yl)-3-buten-2-one (α-ionone), 3-methyl-4-(2,6,6-trimethyl-1-cyclohexen-1-yl)-3-buten-2-one (δ-methyl ionone), 4-(2,6, 6-trimethyl—2-cyclohexen-1-yl)-3-methyl-3-buten-2-one (γ-methyl ionone), 3-methyl-4-(2,6,-trimethyl-2-cyclohexen-1-yl)-3-buten-2-one (irisantheme), 4-(2,3,5-trimethyl-4-cyclohexen-1-yl)-3-buten-2-one (iritone), 4-methyl-(2,5,6,6-tetramethyl-2-cyclohexen-1-yl)-3-buten-2-one (α-ionone), 1,2,3,4,5,6,7,8-octahydro-2,3,8,8-tetramethyl-2-acetonaphthone (iso cyclomone e), 7-acetyl-1,2,3,4,5,6,7,8-octahydro-1,1,6,7-tetramethyl naphthalene (Iso E Super®), acetyl diisoamylene (Koavone®), methyl amyl ketone, 2-acetonaphthone cedr-8-enyl methyl ketone (methyl cedrylone), 2,3,6-trimethyl-cyclohexen-4-yl 1-methyl ketone (methyl cyclo citrone), hexahydroacetophenone (methyl cyclohexyl ketone), 6-methyl-3,5-heptadien-2-one, 6-methyl-5-hepten-2-one, 2-octanoe, 3-(hydroxymethyl)-2-nonanone, 4-acetyl-1,1-dimethyl-6-tert-butyl indane (musk indanone), 2,6-dinitro-3,5-dimethyl-4-acetyl-tert-butyl benzene (musk ketone), 1-para-menthen-6-yl propanone (nerone), para-methoxy acetophenone (acetanisole), 6-acetyl-1,1,2,3,3,5-hexamethyl indan (Phantolid®), 7-acetyl-1,1,3,4,4,6-hexamethyl tetralin (Tonalid®, Musk Plus®), 5-acetyl-3-isopropyl-1,1,2,6-tetramethyl indane (Traseolide 70®), methyl-2,6,10-trimethyl-2,5,9-cyclododecatriene-1-yl ketone (Trimofix O®), methyl cedrylone (Vertofix Coeur®), 4-(4-hydroxy-3-methoxyphenyl)-2-butanone, cis-jasmone, dihydrojasmone, α-ionone, β-ionone, dihydro-β-ionone, 4-(4-hydroxyphenyl)butan-2-one, 1-carvone, 5-cyclohexadecen-1-one, decatone, 2-[2-(4-methyl-3-cyclohexenyl-1-yl) propyl]cyclopentan-2-one, 2-sec-butylcyclohexanone, allyl ionone, α-cetone, geranyl acetate, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, menthone, methyl-7,3-dihydro-2H-1,5-benzodioxepine-3-one, fenchone, methyl hydroxynaphthyl ketone, and mixtures thereof.

According to the present invention all isomers of a fragrance raw material whether in the form of the pro-fragrance or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R-(+)-β-citronellol and S-(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers impart. By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-fragrance which releases d-carvone will result in a different scent or fragrance than one which releases l-carvone. The same applies to l-carvone. In addition, isomers such as cis/trans isomers, for example, nerol (3,7-dimethyl-cis- 2,6-octadien-1-ol) and geraniol (3,7-dimethyl-trans-2,6-octadien-1-ol), are well known to those skilled in the art of perfumery and these two terpene alcohols, which commonly occur as an admixture, have different fragrance characteristics. Therefore, when formulating fragrance raw materials which comprise mixtures of isomers such as nerol/geraniol, the formulator must also take into account whether different sources of raw material have different ratios of isomers.

An example of a preferred pro-fragrance is 3,7-dimethyl-1,6-octadien-3-yl 3-(β-naphthyl)-3-oxo-propionate having the formula:

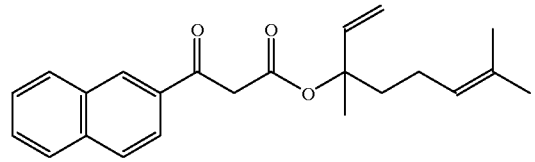

which releases at least the fragrance raw material alcohol, linalool, having the formula:

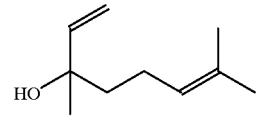

and the fragrance raw material ketone, methyl naphthyl ketone, having the formula:

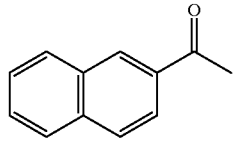

A further example of a preferred pro-fragrance includes 2,6-dimethyl-7-octen-2-yl 3-(4-methoxyphenyl)-3-oxo-propionate having the formula:

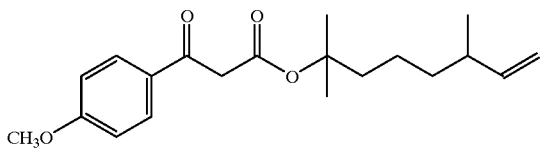

which releases at least the fragrance raw material alcohol, dihydromyrcenol, having the formula:

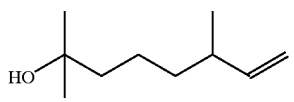

and the fragrance raw material ketone, methyl 4-methoxyphenyl ketone, having the formula:

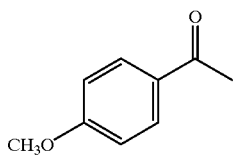

Further non-limiting examples of preferred pro-fragrances include 3,7-dimethyl-1,6-octadien-3-yl 3-(α-naphthyl)-3-oxo-propionate, [linalyl (1-naphthoyl)acetate], having the formula:

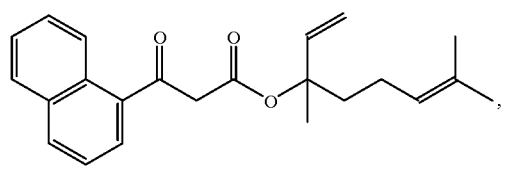

2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

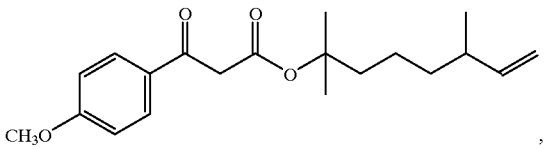

2,6-dimethyl-7-octen-2-yl 3-(4-nitrophenyl)-3-oxo-propionate, [3-(4-nitrophenyl)-3-oxo-propionic acid dihydromyrcenyl ester], having the formula:

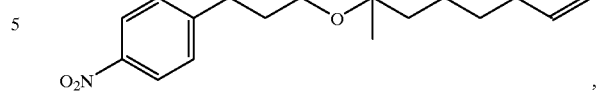

2,6-dimethyl-7-octen-2-yl 3-(P-naphthyl)-3-oxo-propionate, [dihydromyrcenyl (2-naphthoyl)acetate], having the formula:

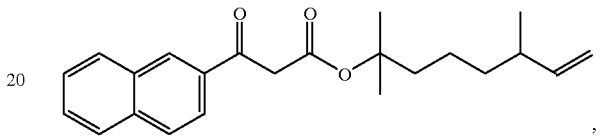

3,7-dimethyl-1,6-octadien-3-yl 3-(4-methoxyphenyl)-3-oxo-propionate, [3-(4-methoxyphenyl)-3-oxo-propionic acid linalyl ester], having the formula:

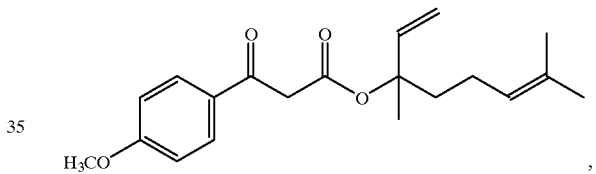

(α,α-4-trimethyl-3-cyclohexenyl)methyl 3-(β-naphthyl)-3-oxo-propionate, [α-terpinyl (2-naphthoyl)acetate], having the formula:

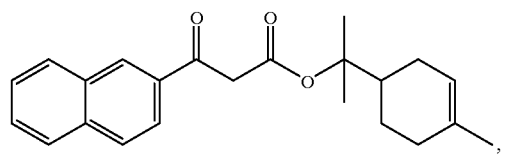

9-decen-1-yl 3-(β-naphthyl)-3-oxo-propionate, [9-decen-1-yl (2-naphthoyl)acetate], known alternatively as, rosalva 2'-acetonaphthone, having the formula:

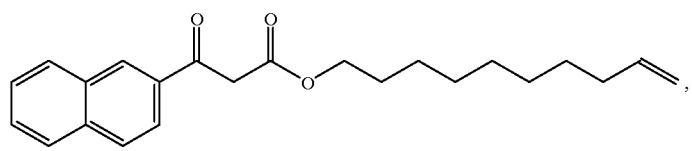

3,7-dimethyl-1,6-octadien-3-yl 3-(nonanyl)-3-oxo-propionate, [linalyl (nonanoyl)acetate], known alternatively as, octyl [(linalyl) (α-acetyl] ketone, having the formula:

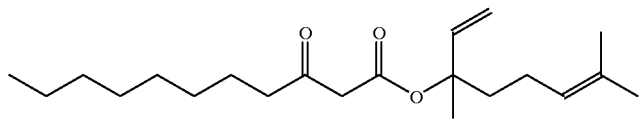

Additional non-limiting examples of preferred pro-fragrances which comprise the fragrance delivery systems of the present invention include cis 3-hexen-1-yl 3-(β-naphthyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(P-naphthyl)-3-oxo-propionate, 3,7-dimethyl-2,6-octadienyl 3-heptyl-3-oxo-propionate, and mixtures thereof.

The formulator is not limited to the delivery of one type of fragrance, for example a top, middle, or base fragrance raw material note. Instead a mixture of top notes, a mixture of top and middle notes, or any combination of top, middle and base notes may be delivered in any suitable proportion.

As described herein above, those skilled in the art of preparing fragrance-containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfumes and fragrances are inter alia "rose", "floral", "green", "citrus", "spicy", "honey", and "musk". The sources of these notes are not limited to one chemical class; alcohols can produce "rose", "green", and "musk" scents, while "rose" scents can comprise alcohols, ketones, terpenes, aldehydes, etc.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. The compositions described herein below, as well as others chosen by the formulator, comprise a fragrance delivery system which utilizes the pro-fragrances of the present invention to successfully deliver a "balanced fragrance" profile.

It is also recognized by those skilled in the art that descriptors which relate to aesthetic perceptions such as "top", "middle" and "base" notes are relative terms. A fragrance raw material categorized as a top note by one formulator usually has the identical classification among most other Perfumers. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a fragrance delivery system which is used to deliver a scent to a laundry detergent composition must meet a number of technical requirements. It must be sufficiently strong, it must be persistent, and it must retain its "essential character" throughout its period of evaporation and fragrance raw material release.

Aside from the changes made to the "pro-fragrance" molecules for the purpose of modifying the fragrance profiles which the fragrance delivery systems of the present invention provide, modifications can be made to these pro-fragrances for the purpose of increasing the substantivity of the materials. The formulator by selecting a suitable $R^1$, $R^2$, or $R^3$ unit, or upon the selection of $R^4$ $R^5$, and $R^6$, can influence the degree and rate at which the "pro-fragrance" is deposited upon fabric or other surface. Those skilled in the art of formulating detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

An example of a pro-fragrance which is modified to provide higher fabric substantivity is the 2,6-dimethyl-7-octen-2-yl 3-(β-naphthyl)-2-(methoxy-pentaethyleneoxy)-3-oxo-propionate, [dihydromyrcenyl (2-naphthoyl)(2-$E_5$ methoxy)acetate], having the formula:

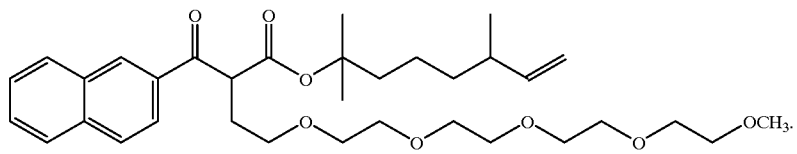

In addition to substitution at the α-carbon atom, substitution can be made at other sites of the pro-accord molecule, for example, 3,7-dimethyl-1,6-octadien-3-yl 3-(methoxy triethyleneoxy)-3-oxo-butyrate, [linalyl (methoxy E₃)acetate] having the formula:

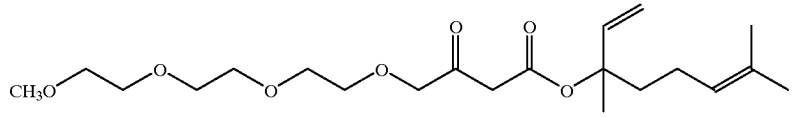

is a pro-fragrance modified to increase fabric substantivity.

Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on wet fabrics. As the water is being removed however, e.g., the fabric is being dried off, some low molecular weight organic amines and acids have more affinity and will complex with the cyclodextrins more readily.

The cavities within the cyclodextrin in the solution of the present invention should remain essentially unfilled (the cyclodextrin remains uncomplexed) while in solution, in order to allow the cyclodextrin to absorb various odor molecules when the solution is applied to a surface. Non-derivatised (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatised beta-cyclodextrin is generally not preferred when the composition contains surfactant since it affects the surface activity of most of the preferred surfactants that are compatible with the derivatized cyclodextrins.

Preferably, the odor absorbing solution of the present invention is clear. The term "clear" as defined herein means transparent or translucent, preferably transparent, as in "water clear," when observed through a layer having a thickness of less than about 10 cm.

Preferably, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —CH₂—CH(OH)—CH₃ or a —CH₂CH₂—OH group; branched cyclodextrins such as maltose-bonded cyclodextrins; cationic cyclodextrins such as those containing 2-hydroxy-3-(dimethylamino)propyl ether, wherein R is CH₂—CH(OH)—CH₂—N(CH₃)₂ which is cationic at low pH; quaternary ammonium, e.g., 2-hydroxy-3-(trimethylammonio) propyl ether chloride groups, wherein R is CH₂—CH(OH)—CH₂—N⁺(CH₃)₃Cl⁻; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3–6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. No: 3,426,011, Parmerter et al., issued Feb. 4, 1969; U.S. Pat. No. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is essential for effective and efficient odor control performance. Solubilized, water-soluble cyclodextrin can exhibit more efficient odor control performance than non-water-soluble cyclodextrin when deposited onto surfaces, especially fabric.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about I to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar USA, Inc, and Wacker Chemicals (USA), Inc.

It is also preferable to use a mixture of cyclodextrins. Such mixtures absorb odors more broadly by complexing with a wider range of odoriferous molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

For controlling odor on fabrics, the composition is preferably used as a spray. It is preferable that the usage compositions of the present invention contain low levels of cyclodextrin so that a visible stain does not appear on the fabric at normal usage levels. Preferably, the solution used to treat the surface under usage conditions is virtually not discernible when dry. Typical levels of cyclodextrin in usage compositions for usage conditions are from about 0.01% to about 5%, preferably from about 0.1% to about 4%, more preferably from about 0.5% to about 2% by weight of the composition. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per gram of fabric, more preferably less than about 2 mg of cyclodextrin per gram of fabric. The presence of the surfactant can improve appearance by minimizing localized spotting.

Concentrated compositions can also be used in order to deliver a less expensive product. When a concentrated product is used, i.e., when the level of cyclodextrin used is from about 3% to about 20%, more preferably from about 5% to about 10%, by weight of the concentrated composition, it is preferable to dilute the concentrated composition before treating fabrics in order to avoid staining. Preferably the concentrated cyclodextrin composition is diluted with about 50% to about 6000%, more preferably with about 75% to about 2000%, most preferably with about 100% to about 1000% by weight of the concentrated composition of water. The resulting diluted compositions have usage concentrations of cyclodextrin as discussed hereinbefore, e.g., of from about 0.1% to about 5%, by weight of the diluted composition.

Surfactant

The cyclodextrin-compatible surfactant, provides a low surface tension that permits the composition to spread readily and more uniformly on hydrophobic surfaces like polyester and nylon. It has been found that the aqueous solution, without such a surfactant will not spread satisfactorily. The spreading of the composition also allows it to dry faster, so that the treated material is ready to use sooner. Furthermore, the composition containing a cyclodextrin-compatible surfactant can penetrate hydrophobic, oily soil better for improved malodor control. The composition containing a cyclodextrin-compatible surfactant also provides improved "in-wear" electrostatic control. For concentrated compositions, the surfactant facilitates the dispersion of many actives such as antimicrobial actives and perfumes in the concentrated aqueous compositions.

The surfactant for use in providing the required low surface tension in the composition of the present invention should be cyclodextrin-compatible, that is it should not substantially form a complex with the cyclodextrin so as to diminish performance of the cyclodextrin and/or the surfactant. Complex formation diminishes both the ability of the cyclodextrin to absorb odors and the ability of the surfactant to lower the surface tension of the aqueous composition.

Suitable cyclodextrin-compatible surfactants can be readily identified by the absence of effect of cyclodextrin on the surface tension provided by the surfactant. This is achieved by determining the surface tension (in dyne/cm$^2$) of aqueous solutions of the surfactant in the presence and in the absence of about 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin. The preferred surfactants herein should have a surface tension in an aqueous solution that is different (lower) by less than about 10%, preferably less than about 5%, and more preferably less than about 1% from that of the same concentration solution containing 1% cyclodextrin.

Nonlimiting examples of cyclodextrin-compatible nonionic surfactants include block copolymers of ethylene oxide and propylene oxide. Suitable block polyoxyethylene-polyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible surfactants of this type include:

Pluronic Surfactants with the general formula:

wherein EO is an ethylene oxide group, PO is a propylene oxide group, and n and m are numbers that indicate the average number of the groups in the surfactants. Typical examples of cyclodextrin-compatible Pluronic surfactants are:

| Name  | Average MW | Average n | Average m |
|-------|-----------|-----------|-----------|
| L-101 | 3,800     | 4         | 59        |
| L-81  | 2,750     | 3         | 42        |
| L-44  | 2,200     | 10        | 23        |
| L-43  | 1,850     | 6         | 22        |
| F-38  | 4,700     | 43        | 16        |
| P-84  | 4,200     | 19        | 43        | and mixtures of said surfactants

Tetronic Surfactants with the general formula:

wherein EO, PO, n, and m have the same meanings as above. Typical examples of cyclodextrin-compatible Tetronic surfactants are:

| Name | Average MW | Average n | Average m |
|------|-----------|-----------|-----------|
| 901  | 4,700     | 3         | 18        |
| 908  | 25,00     | 114       | 22        | also suitable are mixtures thereof.

"Reverse" Pluronic and Tetronic surfactants have the following general formulas:

Reverse Pluronic Surfactants having the formula:

H(PO)$_m$(EO)$_n$(PO)$_m$H

Reverse Tetronic Surfactants having the formula:

wherein EO, PO, n, and m have the same meanings as above. Typical examples of cyclodextrin-compatible Reverse Pluronic and Reverse Tetronic surfactants are:

| Name | Average MW | Average n | Average m |
|------|-----------|-----------|-----------|
| Reverse Pluronic surfactants | | | |
| 10 R5 | 1,950 | 8 | 22 |
| 25 R1 | 2,700 | 21 | 6 |
| Reverse Tetronic surfactants | | | |
| 130 R2 | 7,740 | 9 | 26 |
| 70 R2  | 3,870 | 4 | 13 |

A preferred class of cyclodextrin-compatible nonionic surfactants are the polyalkyleneoxide polysiloxanes having a dimethyl polysiloxane hydrophobic moiety and one or more hydrophilic polyalkylene side chains. Examples of this type of surfactants are the Silwet® surfactants which are available OSi Specialties, Inc., Danbury, Conn., and have the general formula:

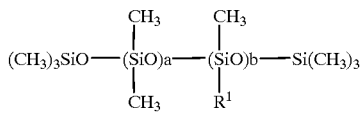

wherein a+b are from about 1 to about 50, preferably from about 3 to about 30, more preferably from about 10 to about 25, and $R^1$ is mainly one or more random poly (ethyleneoxide/propyleneoxide) copolymer groups having the general formula:

—(CH$_2$)$_n$O(C$_2$H$_4$O)$_c$(C$_3$H$_6$O)$_d$R$^2$ wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group.

Representative Silwet surfactants are as follows.

| Name   | Average MW | Average n | Average m |
|--------|-----------|-----------|-----------|
| L-7608 | 600       | 1         | 9         |
| L-7607 | 1,000     | 2         | 17        |
| L-77   | 600       | 1         | 9         |
| L-7605 | 6,000     | 20        | 99        |
| L-7604 | 4,000     | 21        | 53        |
| L-7600 | 4,000     | 11        | 68        |
| L-7657 | 5,000     | 20        | 76        |
| L-7602 | 3,000     | 20        | 29        |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units (—C$_2$H$_4$O) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7657, and mixtures thereof. Besides surface activity, polyalkyleneoxide polysiloxane surfactants can also provide other benefits, such as antistatic benefits, lubricity and softness to fabrics.

The preparation of polyalkyleneoxide polysiloxanes is well known in the art. Polyalkyleneoxide polysiloxanes of the present invention can be prepared according to the procedure set forth in U.S. Pat. No. 3,299,112, incorporated herein by reference. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

Nonlimiting examples of cyclodextrin-compatible anionic surfactants are the alkyldiphenyl oxide disulfonate, having the general formula:

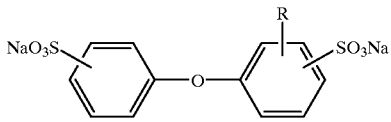

wherein R is an alkyl group, Examples of this type of surfactants are available from the Dow Chemical Company under the trade name Dowfax® wherein R is a linear or branched $C_6$–$C_{16}$ alkyl group. An example of these cyclodextrin-compatible anionic surfactant is Dowfax 3B2 with R being approximately a linear $C_{10}$ group. These anionic surfactants are preferably not used when the antimicrobial active or preservative, etc., is cationic to minimize the interaction with the cationic actives, since the effect of both surfactant and active are diminished. The surfactants above are either weakly interactive with cyclodextrin (less than 5% elevation in surface tension, or non-interactive (less than 1% elevation in surface tension). Normal surfactants like sodium dodecyl sulfate and dodecanolpoly(6)ethoxylate are strongly interactive, with more than a 10% elevation in surface tension in the presence of a typical cyclodextrin like hydroxypropylbeta-cyclodextrin and methylated beta-cyclodextrin.

Typical levels of cyclodextrin-compatible surfactants in usage compositions are from about 0.01% to about 2%, preferably from about 0.03% to about 0.6%, more preferably from about 0.05% to about 0.3%, by weight of the composition. Typical levels of cyclodextrin-compatible surfactants in concentrated compositions are from about 0.1% to about 8%, preferably from about 0.2% to about 4%, more preferably from about 0.3% to about 3%, by weight of the concentrated composition.

Cyclodextrin-compatible Antimicrobial Actives

The solubilized, water-soluble antimicrobial actives useful in providing protection against organisms that become attached to the treated material. The antimicrobial should be cyclodextrin-compatible, e.g., not substantially forming complexes with the cyclodextrin in the odor absorbing composition. The free, uncomplexed antimicrobial, e.g., antibacterial, active provides an optimum antibacterial performance.

Sanitization of fabrics can be achieved by the compositions of the present invention containing, antimicrobial materials, e.g., antibacterial halogenated compounds, quaternary compounds, and phenolic compounds.

Biguanides. Some of the more robust cyclodextrin-compatible antimicrobial halogenated compounds which can function as disinfectants/sanitizers as well as finish product preservatives (vide infra), and are useful in the compositions of the present invention include 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a sanitizer in the present invention it is typically present at a level of from about 0.001% to about 0.4%, preferably from about 0.002% to about 0.3%, and more preferably from about 0.05% to about 0.2%, by weight of the usage composition. In some cases, a level of from about 1% to about 2% may be needed for virucidal activity.

Other useful biguanide compounds include Cosmoci® CQ®, Vantocil® IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane) dihydrochloride; 1,6-di-($N_1,N_1$'-phenyldiguanido-$N_5,N_5$')-hexane tetrahydrochloride; 1,6-di-($N_1,N_1$'-phenyl-$N_1,N_1$'-methyldiguanido-$N_5,N_5$')-hexane dihydrochloride; 1,6-di ($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di[$N_1,N_1$'-beta-(p-methoxyphenyl) diguanido-$N_5,N_5$']-hexane dihydrochloride; 1,6-di($N_1,N_1$'-alpha.-methyl-.beta.-phenyldiguanido-$N_5,N_5$')-hexane dihydrochloride; 1,6-di ($N_1,N_1$'-p-nitrophenyldiguanido-$N_5,N_5$')hexane dihydrochloride;.omega.:.omega.'-di-($N_1,N_1$'-phenyldiguanido-$N_5,N_5$')-di-n-propylether dihydrochloride;.omega:omega'-di($N_1,N_1$'-p-chlorophenyldiguanido-$N_5,N_5$')-di-n-propylether tetrahydrochloride; 1,6-di($N_1,N_1$'-2,4-dichlorophenyldiguanido-$N_5,N_5$')hexane tetrahydrochloride; 1,6-di($N_1,N_1$'-p-methylphenyldiguanido-$N_5,N_5$')hexane dihydrochloride; 1,6-di($N_1,N_1$'-2,4,5-trichlorophenyldiguanido-$N_5,N_5$') hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1$, $N_1$'-p-chlorophenyldiguanido-$N_5,N_5$')m-xylene dihydrochloride; 1,1 2-di($N_1,N_1$'-p-chlorophenyldiguanido-$N_5,N_5$') dodecane dihydrochloride; 1,10-di($N_1,N_1$'-phenyldiguanido-$N_5,N_5$')-decane tetrahydrochloride; 1,12-di($N_1,N_1$'-phenyldiguanido-$N_5$ ,$N_5$') dodecane tetrahydrochloride; 1,6-di($N_1,N_1$'-o-chlorophenyldiguanido-$N_5,N_5$') hexane dihydrochloride; 1,6-di($N_1,N_1$'-p-chlorophenyldiguanido-$N_5,N_5$')-hexane tetrahydrochloride; ethylene bis (1-tolyl biguanide); ethylene bis (p-tolyl biguanide); ethylene bis(3, 5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis (phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1,N_1$'-phenyldiguanido-$N_5,N_5$')-hexane tetrahydrochloride; 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1$, $N_1$'-p-chlorophenyldiguanido-$N_5$,$N_5$')m-xylene dihydrochloride; 1,1 2-di($N_1$,$N_1$'-p-chlorophenyldiguanido-$N_5$,$N_5$') dodecane dihydrochloride; 1,6-di($N_1$,$N_1$'-o-chlorophenyldiguanido-$N_5$,$N_5$') hexane dihydrochloride; 1,6-di($N_1$,$N_1$'-p-chlorophenyldiguanido-$N_5$,$N_5$')-hexane tetrahydrochloride; and mixtures thereof; more preferably, 1,6-di($N_1$,$N_1$'-o-chlorophenyldiguanido-$N_5$,$N_5$')-hexane dihydrochloride; 1,6-di($N_1$,$N_1$'-2,6-dichlorophenyldiguanido-$N_5$,$N_5$')hexane dihydrochloride; 1,6-di($N_1$,$N_1$'-2,4-dichlorophenyldiguanido-$N_5$,$N_5$')hexane tetrahydrochloride; 1,6-di[$N_1$,$N_1$'-.alpha.-(p-chlorophenyl)ethyldiguanido-$N_5$,$N_5$'] hexane dihydrochloride;.omega.:.omega.'di($N_1$, $N_1$'-p-chlorophenyldiguanido-$N_5$,$N_5$')m-xylene dihydrochloride; 1,12-di($N_1$,$N_1$'-p-chlorophenyldiguanido-$N_5$,$N_5$') dodecane dihydrochloride; 1,6-di($N_1$,$N_1$'-o-chlorophenyldiguanido-$N_5$,$N_5$') hexane dihydrochloride; 1,6-di($N_1$,$N_1$'-p-chlorophenyldiguanido-$N_5$,$N_5$')-hexane tetrahydrochloride; and mixtures thereof. As stated hereinbefore, the bis biguanide of choice is chlorhexidine its salts, e.g., digluconate, dihydrochloride, diacetate, and mixtures thereof.

Quaternary Compounds. A wide range of quaternary compounds can also be used as antimicrobial actives, in conjunction with the preferred surfactants, for compositions of the present invention that do not contain cyclodextrin. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) dialkyl quaternary such as Bardac® products of Lonza, (3) N-(3-chloroallyl) hexaminium chlorides such as Dowicide® and Dowicil® available from Dow; (4) benzethonium chloride such as Hyarnine® 1622 from Rohm & Haas; (5) methylbenzethonium chloride represented by Hyamine® 10X supplied by Rohm & Haas, (6) cetylpyridinium chloride such as Cepacol chloride available from of Merrell Labs. Typical concentrations for biocidal effectiveness of these quaternary compounds range from about 0.001% to about 0.8%, preferably from about 0.005% to about 0.3%, more preferably from about 0.01% to 0.2%, by weight of the usage composition. The corresponding concentrations for the concentrated compositions are from about 0.003% to about 2%, preferably from about 0.006% to about 1.2%, and more preferably from about 0.1% to about 0.8% by weight of the concentrated compositions.

The surfactants, when added to the antimicrobials tend to provide improved antimicrobial action. This is especially true for the siloxane surfactants, and especially when the siloxane surfactants are combined with the chlorhexidine antimicrobial actives.

Low Molecular Weight Polyols

Low molecular weight polyols with relatively high boiling points, as compared to water, such as ethylene glycol, propylene glycol and/or glycerol are preferred optional ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the fabric dries.

It is believed that the polyols' ability to remain on the fabric for a longer period of time than water, as the fabric dries allows it to form ternary complexes with the cyclodextrin and some malodorous molecules. The addition of the glycols is believed to fill up void space in the cyclodextrin cavity that is unable to be filled by some malodor molecules of relatively smaller sizes. Preferably the glycol used is glycerine, ethylene glycol, propylene glycol, dipropylene glycol or mixtures thereof, more preferably ethylene glycol and propylene glycol. Cyclodextrins prepared by processes that result in a level of such polyols are highly desirable, since they can be used without removal of the polyols.

Some polyols, e.g., dipropylene glycol, are also useful to facilitate the solubilization of some perfume ingredients in the composition of the present invention.

Typically, glycol is added to the composition of the present invention at a level of from about 0.01% to about 3%, by weight of the composition, preferably from about 0.05% to about 1%, more preferably from about 0.1% to about 0.5%, by weight of the composition. The preferred weight ratio of low molecular weight polyol to cyclodextrin is from about 2:1,000 to about 20:100, more preferably from about 3:1,000 to about 15:100, even more preferably from about 5:1,000 to about 10:100, and most preferably from about 1:100 to about 7:100.

Aminocarboxylate Chelators

Chelators, e.g., ethylenediaminetetraacetic acid (EDTA), hydroxyethylene-diaminetriacetic acid, diethylenetriamine-pentaacetic acid, and other aminocarboxylate chelators, and mixtures thereof, and their salts, and mixtures thereof, can optionally be used to increase antimicrobial and preservative effectiveness against Gram-negative bacteria, especially Pseudomonas species. Although sensitivity to EDTA and other aminocarboxylate chelators is mainly a characteristic of Pseudomonas species, other bacterial species highly susceptible to chelators include Achromobacter, Alcaligenes, Azotobacter, Escherichia, Salmonella, Spirillum, and Vibrio. Other groups of organisms also show increased sensitivities to these chelators, including fungi and yeasts. Furthermore, aminocarboxylate chelators can help, e.g., maintaining product clarity, protecting fragrance and perfume components, and preventing rancidity and off odors.

Although these aminocarboxylate chelators may not be potent biocides in their own right, they function as potentiators for improving the performance of other antimicrobials/preservatives in the compositions of the present invention. Aminocarboxylate chelators can potentiate the performance of many of the cationic, anionic, and nonionic antimicrobials/preservatives, phenolic compounds, and isothiazolinones, that are used as antimicrobials/preservatives in the composition of the present invention. Nonlimiting examples of cationic antimicrobials/preservatives potentiated by aminocarboxylate chelators in solutions are chlorhexidine salts (including digluconate, diacetate, and dihydrochloride salts), and Quaternium-15, also known as Dowicil 200, Dowicide Q, Preventol D1, benalkonium chloride, cetrimonium, myristalkonium chloride, cetylpyridinium chloride, lauryl pyridinium chloride, and the like. Nonlimiting examples of useful anionic antimicrobials/preservatives which are enhanced by aminocarboxylate chelators are sorbic acid and potassium sorbate. Nonlimiting examples of useful nonionic antimicrobials/preservatives which are potentiated by aminocarboxylate chelators are DMDM hydantoin, phenethyl alcohol, monolaurin, imidazolidinyl urea, and Bronopol (2-bromo-2-nitropropane-1,3-diol).

Examples of useful phenolic antimicrobials/preservatives potentiated by these chelators are chloroxylenol, phenol, tert-butyl hydroxyanisole, salicylic acid, resorcinol, and sodium o-phenyl phenate. Nonlimiting examples of isothiazolinone antimicrobials/preservatives which are enhanced by aminocarboxylate chelators are Kathon, Proxel and Promexal.

The optional chelators are present in the compositions of this invention at levels of, typically, from about 0.01% to about 0.3%, more preferably from about 0.02% to about 0.1%, most preferably from about 0.02% to about 0.05% by weight of the usage compositions to provide antimicrobial efficacy in this invention.

Free, uncomplexed aminocarboxylate chelators are required to potentiate the efficacy of the antimicrobials. Thus, when excess alkaline earth (especially calcium and magnesiumn) and transitional metals (iron, manganese, copper, and others) are present, free chelators are not available and antimicrobial potentiation is not observed. In the case where significant water hardness or transitional metals are available or where product esthetics require a specified chelator level, higher levels may be required to allow for the availability of free, uncomplexed aminocarboxylate chelators to function as antimicrobial/preservative potentiators.

Metal Salts

Optionally, but highly preferred, the present invention can include metallic salts for added odor absorption and/or antimicrobial benefit for the cyclodextrin solution. The metallic salts are selected from the group consisting of copper salts, zinc salts, and mixtures thereof.

Copper salts have some antimicrobial benefits. Specifically, cupric abietate acts as a fungicide, copper acetate acts as a mildew inhibitor, cupric chloride acts as a fungicide, copper lactate acts as a fungicide, and copper sulfate acts as a germicide. Copper salts also possess some malodor control abilities. See U.S. Pat. No. 3,172,817, Leupold, et al., which discloses deodorizing compositions for treating disposable articles, comprising at least slightly water-soluble salts of acylacetone, including copper salts and zinc salts, all of said patents are incorporated herein by reference.

The preferred zinc salts possess malodor control abilities. Zinc has been used most often for its ability to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., all of which are incorporated herein by reference. Highly-ionized and soluble zinc salts such as zinc chloride, provide the best source of zinc ions. Zinc borate functions as a fungistat and a mildew inhibitor, zinc caprylate functions as a fungicide, zinc chloride provides antiseptic and deodorant benefits, zinc ricinoleate functions as a fungicide, zinc sulfate heptahydrate functions as a fungicide and zinc undecylenate functions as a fungistat.

Preferably the metallic salts are water-soluble zinc salts, copper salts or mixtures thereof, and more preferably zinc salts, especially $ZnCl_2$. These salts are preferably present in the present invention primarily to absorb amine and sulfur-containing compounds that have molecular sizes too small to be effectively complexed with the cyclodextrin molecules. Low molecular weight sulfur-containing materials, e.g., sulfide and mercaptans, are components of many types of malodors, e.g., food odors (garlic, onion), body/perspiration odor, breath odor, etc. Low molecular weight amines are also components of many malodors, e.g., food odors, body odors, urine, etc.

When metallic salts are added to the composition of the present invention they are typically present at a level of from about 0.1% to about 10%, preferably from about 0.2% to about 8%, more preferably from about 0.3% to about 5% by weight of the usage composition. When zinc salts are used as the metallic salt, and a clear solution is desired, it is preferable that the pH of the solution is adjusted to less than about 7, more preferably less than about 6, most preferably, less than about 5, in order to keep the solution clear.

Carriers

Aqueous solutions are preferred for odor control. The dilute aqueous solution provides the maximum separation of cyclodextrin molecules on the fabric and thereby maximizes the chance that an odor molecule will interact with a cyclodextrin molecule.

The preferred carrier of the present invention is water. The water which is used can be distilled, deionized, or tap water. Water not only serves as the liquid carrier for the cyclodextrins, but it also facilitates the complexation reaction between the cyclodextrin molecules and any malodorous molecules that are on the fabric when it is treated. It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

Perfume

The odor absorbing composition of the present invention can also optionally provide a "scent signal" in the form of a pleasant odor which signals the removal of malodor from fabrics. The scent signal is designed to provide a fleeting perfume scent, and is not designed to be overwhelming or to be used as an odor masking ingredient. When perfume is added as a scent signal, it is added only at very low levels, e.g., from about 0% to about 0.5%, preferably from about 0.003% to about 0.3%, more preferably from about 0.005% to about 0.2%, by weight of the usage composition.

Perfume can also be added as a more intense odor in product and on surfaces. When stronger levels of perfume are preferred, relatively higher levels of perfume can be added. Any type of perfume can be incorporated into the composition of the present invention. It is essential, however, that the perfume be added at a level wherein even if all of the perfume in the composition were to complex with the cyclodextrin molecules, there will still be an effective level of uncomplexed cyclodextrin molecules present in the solution to provide adequate odor control. In order to reserve an effective amount of cyclodextrin molecules for odor control, perfume is typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio should be greater than about 8:1, preferably greater than about 10:1, more preferably greater than about 20:1, even more preferably greater than 40:1 and most preferably greater than about 70:1.

Preferably the perfume is hydrophilic and is composed predominantly of ingredients selected from two groups of ingredients, namely, (a) hydrophilic ingredients having a ClogP of less than about 3.5, more preferably less than about 3.0, and (b) ingredients having significant low detection threshold, and mixtures thereof. Typically, at least about 50%, preferably at least about 60%, more preferably at least about 70%, and most preferably at least about 80% by weight of the perfume is composed of perfume ingredients of the above groups (a) and (b). For these preferred perfumes, the cyclodextrin to perfume weight ratio is typically of from about 2:1 to about 200:1; preferably from about 4:1 to about 100:1, more preferably from about 6:1 to about 50:1, and even more preferably from about 8:1 to about 30:1.

(a). Hydrophilic Perfume Ingredients

The hydrophilic perfume ingredients are more soluble in water, have less of a tendency to complex with the cyclodextrins, and are more available in the odor absorbing composition than the ingredients of conventional perfumes. The degree of hydrophobicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the preferred perfume hydrophilic perfume ingredients of this invention have logP of about 3.5 or smaller, preferably of about 3.0 or smaller.

The logP of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the more preferred hydrophilic perfume ingredients are allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, coumarin, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flor acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, viridine, and mixtures thereof.

Nonlimiting examples of other preferred hydrophilic perfume ingredients which can be used in perfume compositions of this invention are allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, musk ketone, beta naphthol methyl ether, neral, nonyl aldehyde, phenyl heptanol, phenyl hexanol, terpinyl acetate, Veratrol, yara—yara, and mixtures thereof.

The preferred perfume compositions used in the present invention contain at least 4 different hydrophilic perfume ingredients, preferably at least 5 different hydrophilic perfume ingredients, more preferably at least 6 different hydrophilic perfume ingredients, and even more preferably at least 7 different hydrophilic perfume ingredients. Most common perfume ingredients which are derived from natural sources are composed of a multitude of components. When each such material is used in the formulation of the preferred perfume compositions of the present invention, it is counted as one single ingredient, for the purpose of defining the invention.

(b). Low Odor Detection Threshold Perfume Ingredient

The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as hydrophilic as perfume ingredients of group (a) which are given hereinabove. Perfume ingredients that do not belong to group (a) above, but have a significantly low detection threshold, useful in the composition of the present invention, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present at low levels in addition to the hydrophilic ingredients of group (a), typically less than about 20%, preferably less than about 15%, more preferably less than about 10%, by weight of the total perfume compositions of the present invention. However, only low levels are required to provide an effect.

There are also hydrophilic ingredients of group (a) that have a significantly low detection threshold, and are especially useful in the composition of the present invention. Examples of these ingredients are allyl amyl glycolate, anethole, benzyl acetone, calone, cinnamic alcohol, coumarin, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof. Use of low odor detection threshold perfume ingredients minimizes the level of organic material that is released into the atmoshphere.

Adjunct Ingredients

The composition of the present invention can optionally contain adjunct odor-controlling materials, chelating agents, antistatic agents, insect and moth repelling agents, colorants, especially bluing agents, antioxidants, and mixtures thereof in addition to the cyclodextrin molecules. The total level of optional ingredients is low, preferably less than about 5%, more preferably less than about 3%, and even more preferably less than about 1%, by weight of the usage composition. These optional ingredients exclude the other ingredients specifically mentioned hereinbefore. Incorporating adjunct odor-controlling materials can enhance the capacity of the cyclodextrin to control odors as well as broaden the range of odor types and molecule sizes which can be controlled. Such materials include, for example, metallic salts, water-soluble cationic and anionic polymers, zeolites, water-soluble bicarbonate salts, and mixtures thereof.

Water Soluble Polymers

Some water-soluble polymers, e.g., water-soluble cationic polymer and water-soluble anionic polymers can be used in the composition of the present invention to provide additional odor control benefits.

a. Cationic polymers, e.g., polyamines

Water-soluble cationic polymers, e.g., those containing amino functionalities, amido functionalities, and mixtures thereof, are useful in the present invention to control certain acid-type odors.

b. Anionic polymers, e.g., polyacrylic acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphonic acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280(from Calgon.

Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the composition should be essentially free of zinc and other incompatible metal ions, e.g., Ca, Fe, Ba, etc. which form water-insoluble salts.

Antistatic Agents

The composition of the present invention can optionally contain an effective amount of antistatic agent to provide the treated clothes with in-wear static. Preferred antistatic agents are those that are water soluble in at least an effective amount, such that the composition remains a clear solution. Examples of these antistatic agents are monoalkyl cationic quaternary ammonium compounds, e.g., mono($C_{10}$–$C_{14}$ alkyl)trimethyl ammonium halide, such as monolauryl trimethyl ammonium chloride, hydroxycetyl hydroxyethyl dimethyl ammonium chloride, available under the trade name Dehyquart E® from Henkel, and ethyl bis(polyethoxy ethanol) alkylammonium ethylsulfate, available under the trade name Variquat 660 from Witco Corp., polyethylene glycols, polymeric quaternary ammonium salts, such as polymers conforming to the general formula:

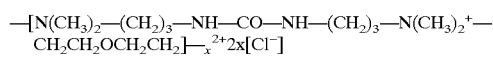

available under the trade name Mirapol A-15® from Rhone-Poulenc, and

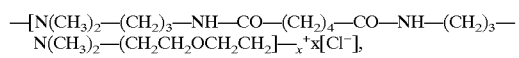

available under the trade name Mirapol AD-1® from Rhone-Poulenc, quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

When an antistatic agent is used it is typically present at a level of from about 0.05% to about 10%, preferably from about 0.1% to about 5%, more preferably from about 0.3% to about 3%, by weight of the usage composition.

Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citronellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696, 676, 4,933,371, 5,030,660, 5,196,200, and in "Semio Activity of Flavor and Fragrance Molecules on Various Insect Species", B. D. Mookherjee et al., published in *Bioactive Volatile Compounds from Plants,* ASC Symposium Series 525, R. Teranishi, R. G. Buttery, and H. Sugisawa, 1993, pp. 35–48, all of said patents and publications being incorporated herein by reference. When an insect and/or moth repellent is used it is typically present at a level of from about 0.005% to about 3%, by weight of the usage composition.

Additional Odor Absorbers

When the clarity of the solution is not needed, and the solution is not sprayed on fabrics, other optional odor absorbing materials, e.g., zeolites and/or activated carbon, can also be used.

Zeolites

A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valforg® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

Activated Carbon

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof.

Optional Preservative

Optionally, but preferably, solubilized, water-soluble, antimicrobial preservative can be added to the composition of the present invention if the antimicrobial material C. is not sufficient, or is not present, because cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth can result in an unsightly and/or malodorous solution. Because microbial growth in cyclodextrin solutions is highly objectionable when it occurs, it is highly preferable to include a solubilized, water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth can be found in the presence of cyclodextrin in aqueous cyclodextrin solutions include bacteria, e.g., *Bacillus thuringiensis* (cereus group) and *Bacillus sphaericus;* and fungi, e.g., *Aspergillus ustus.* *Bacillus sphaericus* is one of the most numerous members of Bacillus species in soils. *Aspergillus ustus* is common in grains and flours which are raw materials to produce cyclodextrins. Microorganisms such as *Escherichia coli* and *Pseudomonas aeruginosa* are found in some water sources, and can be introduced during the preparation of cyclodextrin solutions. Other Pseudomonas species, such as *P. cepacia,* are typical microbial contaminants in surfactant manufacturing facilities and may readily contaminate packed finished products. Typical other bacterial contaminants may include Burkholderia, Enterobacter and Gluconobacter species. Representative fungal species which may be associated with agricultural soils, crops and in the case of this invention, corn products such as cyclodextrins include Aspergillus, Absidia, Penicillium, Paecilomyces, and other species.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the malodorous molecules for the cyclodextrin cavities, thus rendering the cyclodextrins ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative in the present invention is included at an effective amount. The term "effective amount" as herein defined means a level sufficient to prevent spoilage, or prevent growth of inadvertently added microorganisms, for a specific period of time. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.5%, more preferably from about 0.0002% to about 0.2%, most preferably from about 0.0003% to about 0.1%, by weight of the usage composition.

In order to reserve most of the cyclodextrins for odor control, the cyclodextrin to preservative molar ratio should be greater than about 5:1, preferably greater than about 10:1, more preferably greater than about 50:1, even more preferably greater than about 100:1.

The preservative can be any organic preservative material which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The following are non-limiting examples of preferred water-soluble preservatives for use in the present invention.

Organic Sulfur Compounds

Preferred water-soluble preservatives for use in the present invention are organic sulfur compounds. Some non-limiting examples of organic sulfur compounds suitable for use in the present invention are:

a 3-Isothiazolone Compounds

A preferred preservative is an antimicrobial, organic preservative Containing 3-isothiazolone groups having the formula:

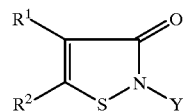

wherein Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a $(C_1–C_4)$ alkyl group; and $R^2$ is hydrogen, halogen, or a $(C_1–C_4)$ alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable.

This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; ; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is present at a level of from about 0.0001% to about 0.01%, preferably from about 0.0002% to about 0.005%, more preferably from about 0.0003% to about 0.003%, most preferably from about 0.0004% to about 0.002%, by weight of the composition.

Other isothiazolins include 1,2-benzisothiazolin-3-one, available under the trade name Proxel® products; and 2-methyl-4,5-trimethylene-4-isothiazolin-3-one, available under the trade name Promexal®. Both Proxel and Promexal are available from Zeneca. They have stability over a wide pH range (i.e., 4–12). Neither contain active halogen and are not formaldehyde releasing preservatives. Both Proxel and Promexal are effective against typical Gram negative and positive bacteria, fungi and yeasts when used at a level from about 0.001% to about 0.5%, preferably from about 0.005% to about 0.05%, and most preferably from about 0.01% to about 0.02% by weight of the usage composition.

b Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the usage composition.

Mixtures of the preferred organic sulfur compounds can also be used as the preservative in the present invention.

Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the usage composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the usage composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorohexidine is used as the preservative in the present invention it is typically present at a level of from about 0.0001% to about 0.04%, preferably from about 0.0005% to about 0.01%, by weight of the usage composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the usage composition.

4,4'-(Trimethylenedioxy)bis-(3-bromobenzamidine) diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the usage composition.

Mixtures of the preferred halogenated compounds can also be used as the preservative in the present invention.

Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2% by weight of the usage composition;

N-[ 1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1% by weight of the usage composition;

N,N"-methylenebis{N'-[1-(hydroxymethyl)-2,5-dioxo-4-imidazolidinyl]urea}, commonly known as imidazolidinyl urea, available, e.g., under the trade name Abiol®V from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the usage composition.

Mixtures of the preferred imidazolidinedione compounds can also be used as the preservative in the present invention.

b) Polymethoxy Bicyclic Oxazolidine

Another preferred water-soluble cyclic organic nitrogen preservative is polymethoxy bicyclic oxazolidine, having the general formula:

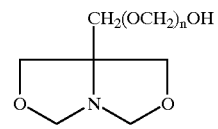

where n has a value of from about 0 to about 5, and is available under the trade name Nuosept® C from Hüls America. When Nuosept® C is used as the preservative, it is typically present at a level of from about 0.005% to about 0.1%, by weight of the usage composition.

Mixtures of the preferred cyclic organic nitrogen compounds can also be used as the preservative in the present invention.

Low Molecular Weight Aldehydes a) Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%. more preferably from about 0.01% to about 0.05%, by weight of the usage composition.

b) Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the usage composition.

Quaternary Compounds

Preferred preservatives for use in the present invention are cationic and/or quaternary compounds. Such compounds include polyaminopropyl biguanide, also known as polyhexamethylene biguanide having the general formula:

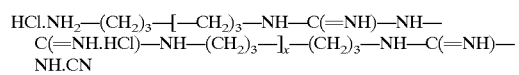

Polyaminopropyl biguanide is a water-soluble, broad spectrum preservative which is available as a 20% aqueous solution available under the trade name Cosmocil CQ® from ICI Americas, Inc., or under the trade name Mikrokill from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the usage composition.

Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the usage composition.

Phenyl and Phenolic Compounds

Some non-limiting examples of phenyl and phenolic compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level of these salts is about 0.0002% to about 0.05% by weight of the usage composition.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the usage composition.

Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11. Low pH for microbial control is not a preferred approach in the present invention because the low pH can cause chemical degradation of the cyclodextrins. High pH for microbial control is also not preferred because at high pH's, e.g., greater than about 10, preferably greater than about 11, the cyclodextrins can be ionized and their ability to complex with organic materials is reduced. Therefore, aqueous compositions of the present invention should have a pH of from about 3 to about 10, preferably from about 4 to about 8, more preferably from about 4.5 to about 6. The pH is typically adjusted with inorganic molecules to minimize complexation with cyclodextrin.

The following examples illustrate the β-keto-esters and compositions of this invention, but are not intended to be limiting thereof.

EXAMPLE 1

Preparation of 3,7-dimethyl-1,6-octadien-3-yl 3-(β-naphthyl)-3-oxo-propionate

Lithium diisopropylamide (101.0 mL of a 2.0 M solution, 0.202 mol) is placed into a 500 mL three-necked round-bottomed flask fitted with a magnetic stirrer, internal thermometer, argon inlet, and addition funnel. The flask is placed in a dry ice-acetone bath. 3,7-Dimethyl-1,6-octadien-3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1$H and $^{13}$C NMR.

EXAMPLE 2

Preparation of 2,6-dimethyl-7-octen-2-yl 3-(4-methoxyphenyl)-3-oxo-propionate

N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition funnel. The flask is placed in a ice-methanol bath cooled to −5° C. and its contents treated with n-butyllithium in the amount of (70.8 mL of a 2.50 M solution, 0.177 mol). The mixture is stirred for 20 min and then cooled to −78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution of p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory funnel containing ether (100 ml) and water (200 ml). The aqueous layer is extracted with ether (100 ml). The combined organic layers are washed with saturated NaHCO$_3$ solution (2×100 ml), water (2×100 ml) and brine (100 ml), dried over MgSO$_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1$H and $^{13}$C NMR.

EXAMPLE 3

Preparation of 2,6-dimethyl-7-octen-2-yl 3-(4-nitrophenyl)-3-oxo-propionate

Lithium diisopropylamide (121.0 mL of a 2.0 M solution, 0.243 mol) is placed into a 500 mL three-necked round-bottomed flask fitted with a magnetic stirrer, internal thermometer, argon inlet, and addition funnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having I H and $^{13}C$ NMR spectra consistent with the desired product.

EXAMPLE 4

Preparation of 2,6-dimethyl-7-octen-2-yl 3-(β-naphthyl)-3-oxo-propionate

Lithium diisopropylamide in the amount of (100.0 mL of a 2.0 M solution, 0.201 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate in the amount of (18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate dissolved in petroleum ether) to give an oil. Purity of the product is determined by thin layer chromatography and the structure confirmed by $^1H$ and $^{13}C$ NMR.

EXAMPLE 5

Preparation of 3,7-dimethyl-1,6-octadien-3-yl 3-(4-methoxyphenyl)-3-oxo-propionate Lithium diisopropylamide (119.0 mL of a 2.0 M solution, 0.238 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution of p-anisoyl chloride (35.00 g, 0.106 mol) dissolved in THF (30 mL) over 30 min. The mixture is warmed to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (150 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 6

Preparation of (α,α-4-trimethyl-3-cyclohexenyl) methyl 3-(β-naphthyl)-3-oxo-propionate Lithium diisopropylamide (171.0 mL of a 2.0 M solution, 0.342 mol) is placed into a 1000 mL three-necked round-bottomed flask fitted with a magnetic stirrer, internal thermometer, argon inlet, and addition funnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (1 05 mL). The mixture is poured into a separatory funnel containing ether (150 mL) and water (250 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1H$ and $^{13}C$ NMR spectra consistent with the desired product.

EXAMPLE 7

Preparation of 3,7-dimethyl-1,6-octadien-3-yl 3-(α-naphthyl)-3-oxo-propionate Lithium diisopropylamide (96.3 mL of a 2.0 M solution, 0.193 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (17.81 g, 0.091 mol) is dissolved in THF (5 mL) and the resulting solution added to the flask over 45 min. Once addition is complete, the mixture is stirred for an additional 15 min. before being treated with a solution of I -naphthoyl chloride (16.82 g, 0.086 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 8

Preparation of cis 3-hexen-1-yl 3-(β-naphthyl)-3-oxo-propionate

Lithium diisopropylamide (133.0 mL of a 2.0 M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature for 18 h. After warming to 0° C., the mixture is quenched with 20% HCl (70 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 9

Preparation of 9-decen-1-yl 3-(β-naphthyl)-3-oxo-propionate

Lithium diisopropylamide (79.8 mL of a 2.0 M solution, 0.160 mol) is placed into a 250 mL three-necked round-bottomed flask fitted with a magnetic stirrer, internal thermometer, argon inlet, and addition funnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 10

Preparation of 3,7-dimethyl-1,6-octadien-3-yl 3-(nonanyl)-3-oxo-propionate

Lithium diisopropylamide (133.7 mL of a 2.0 M solution, 0.267 mol) is placed into a 500 mL three-necked round-bottomed flask fitted with a magnetic stirrer, internal thermometer, argon inlet, and addition funnel. The flask is cooled to −78° C. 3,7-dimethyl-1,6-octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.1 19 mol) over 30 min. The mixture is warmed to −20° C. and stirred at that temperature for 18 h. After warming to 0° C., the mixture is quenched with 20% HCl (60 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 11

Preparation of 2,6-dimethyl-7-octen-2-yl 3-(nonanyl)-3-oxo-propionate

Lithium diisopropylamide (75.7 mL of a 2.0 M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7-octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 12

Preparation of 3,7-dimethyl-1,6-octadien-3-yl 3-oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition funnel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromatography (elution with dichloromethane) yields the desired product in 92% yield and nearly colorless.

EXAMPLE 13

Preparation of 2,6-dimethyl-7-octen-2-yl 3-oxo-butyrate

A mixture of dihydromyrcenol (37.88 g, 0.240 mol) and 4-dimethylaminopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0.240 mol) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14

Preparation of 3,7-dimethyl-1,6-octadien-3-yl 3-(β-naphthyl)-3-oxo-propionate

Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated NaHCO$_3$ solution (2×500 mL), dried over MgSO$_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoyl)acetate. A portion of this material is purified by column chromatography (elution with 2.5% ethyl acetate in hexanes) to give the desired product as a light yellow oil.

EXAMPLE 15

Preparation of 3,7-dimethyl-1,6-octadien-3-yl 3-(β-naphthyl)-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(P-naphthyl)-3-oxo-propionate (8.94 g, 0.025 mol) dissolved in 50 mL of tetrahydrofuran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 16

Preparation of 3,7-dimethyl-1,6-octadien-3-yl 3-(β-naphthyl)-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 17

Preparation of 3,7-dimethyl-1,6-octadien-3-yl 3-(hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated NaHCO$_3$ solution, water, dried over MgSO$_4$, filtered, concentrated by rotary evaporation and purified by flash chromatography to yield the desired compound. Structure is confirmed my $^1$H and $^{13}$C NMR.

EXAMPLE 18

Preparation of 3,7-dimethyl-1,6-octadien-3-yl 3-oxo-2-benzylbutyrate

Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1$H and $^{13}$C NMR.

The following Examples illustrate the present invention.

TABLE I

| Examples Ingredients | 19 Wt. % | 20 Wt. % | 21 Wt. % | 22 Wt. % | 23 Wt. % | 24 Wt. % |
|---|---|---|---|---|---|---|
| HPBCD[1] | 1.0 | — | 0.5 | — | 0.5 | — |
| RAMEB[2] | — | 1.0 | — | 1.0 | — | 1.0 |
| HPACD[3] | — | — | 0.5 | — | 0.5 | — |
| α-Cyclodextrin | — | — | — | — | — | 0.5 |
| Zinc chloride | 1.0 | 1.0 | 1.0 | 1.0 | 1.0 | 0.5 |
| Silwet L-7600 | 0.15 | — | — | — | — | 0.05 |
| Silwet L-7602 | — | 0.4 | — | — | — | — |
| Silwet L-7604 | — | — | 0.2 | — | — | — |
| Silwet L-7605 | — | — | — | 0.2 | — | — |
| Silwet L-7657 | — | — | — | — | 0.15 | — |
| Pro-Fragrance[4] | 0.2 | 0.3 | 0.25 | — | — | — |
| Pro-Fragrance[5] | — | — | — | 0.32 | 0.35 | 0.32 |
| Perfume | 0.05 | — | 0.05 | — | 0.03 | — |
| Propylene glycol | 0.06 | — | — | — | 0.1 | — |
| Kathon CG | 3 ppm | 3 ppm | 3 ppm | 3 ppm | 3 ppm | 3 ppm |
| Hydrochloric acid | to pH 4 | to pH 4 | to pH 4 | to pH 4 | to pH 4 | to pH 4 |
| Distilled water | bal | bal | bal | bal | bal | bal |

[1]Hydroxypropyl β-cyclodextrin.
[2]Randomly methylated β-cyclodextrin.
[3]Hydroxypropyl α-cyclodextrin.
[4]3,7-dimethyl-1,6-octadien-3-yl 3-(β-naphthyl)-3-oxo-propionate.
[5]3,7-dimethyl-1,6-octadien-3-yl 3-oxo-butyrate.

TABLE II

| Examples Ingredients | 25 Wt. % | 26 Wt. % | 27 Wt. % | 28 Wt. % | 29 Wt. % | 30 Wt. % |
|---|---|---|---|---|---|---|
| HPBCD[1] | 1.2 | — | 0.6 | — | 1.0 | — |
| RAMEB[2] | — | 1.0 | — | 0.5 | — | 1.2 |
| α-Cyclodextrin | — | — | 0.4 | 0.5 | — | — |
| ZnCl$_2$ | — | — | 1.0 | 0.5 | — | — |
| CuCl$_2$ | — | — | — | — | 0.3 | — |
| Pluronic L-44 | 0.2 | — | — | — | — | — |
| Pluronic F-38 | — | —0.15 | — | — | — | — |
| Pluronic 25 R1 | — | — | 0.2 | — | — | — |
| Tetronic 901 | — | — | — | 0.2 | — | — |
| Tetronic 70 R2 | — | — | — | — | 0.25 | — |
| Dowfax 3B2 | — | — | — | — | — | 0.15 |
| Pro-fragrance[3] | 0.25 | 0.2 | 0.1 | — | — | 0.15 |
| Pro-fragrance[4] | — | — | 0.15 | 0.2 | 0.3 | — |
| Perfume | — | 0.03 | 0.05 | 0.03 | 0.02 | 0.1 |
| Barquat 4250[5] | 0.03 | — | — | — | — | — |
| Bardac 2050[6] | — | 0.03 | — | — | — | — |
| Chlorhexidine | — | — | 0.05 | 0.02 | 0.01 | — |
| EDTA | — | — | — | 0.05 | 0.02 | — |
| Kathon CG | 3 ppm | 3 ppm | 3 ppm | 3 ppm | 3 ppm | 3 ppm |
| Hydrochloric acid | to pH 4.5 | to pH 4.5 | to pH 3.5 | to pH 3.5 | to pH 3.5 | to pH 4 |
| Distilled water | bal | bal | bal | bal | bal | — |

[1]Hydroxypropyl β-cyclodextrin.
[2]Randomly methylated β-cyclodextrin.
[3]3,7-dimethyl-1,6-octadien-3-yl 3-(β-naphthyl)-3-oxo-propionate.
[4]3,7-dimethyl-1,6-octadien-3-yl 3-oxo-butyrate.
[5]Benzalkonium chloride, 50% solution.
[6]Dioctyl dimethyl ammonium chloride, 50% solution.

What is claimed is:

1. A malodor control composition comprising:
  a) from about 0.01% to about 15% by weight, of a β-ketoester selected from the group consisting of 3,7-dimethyl-1,6-octadien-3-yl 3-(β-naphthyl)-3-oxo-propionate; 2,6-dimethyl-7-octen-2-yl 3-(β-naphthyl)-3-oxo-propionate; 3,7-dimethyl-1,6-octadien-3-yl 3-(4-methoxyphenyl)-3-oxo-propionate; (α,α-4-trimethyl-3-cyclohexenyl)methyl 3-(β-naphthyl)-3-oxo-propionate; 3,7-dimethyl-1,6-octadien-3-yl 3-(α-naphthyl)-3-oxo-propionate; cis 3-hexen-1-yl 3-(β-naphthyl)-3-oxo-propionate, 9-decen-1-yl 3-(β-naphthyl)-3-oxo-propionate; 2,6-dimethyl-7-octen-2-yl 3-oxo-butyrate; 3,7-dimethyl-1,6-octadien-3-yl 3-oxo-butyrate; 2,6-dimethyl-7-octen-2-yl 3-(β-naphthyl)-3-oxo-2-methylpropionate; 3,7-dimethyl-1,6-octadien-3-yl 3-(β-naphthyl)-3-oxo-2,2-dimethylpropionate; 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate; and mixtures thereof;
  b) from about 0.01% to about 15% by weight, of an uncomplexed cyclodextrin; and
  c) the balance carriers and adjunct ingredients.

2. A composition according to claim 1 comprising from about 1% to about 5% by weight, of said β-ketoester.

3. A composition according to claim 2 comprising from about 0.1% to about 1% by weight, of said β-ketoester.

4. A composition according to claim 1 wherein said cyclodextrin is selected from the group consisting of α-cyclodextrin, hydroxypropyl-α-cyclodextrin, hydroxypropyl-β-cyclodextrin, methylated α-cyclodextrin, methylated β-cyclodextrin, and mixtures thereof.

5. A composition according to claim 1 wherein said β-ketoester releases a fragrance raw material alcohol selected from the group consisting of 3,7-dimethyl-1,6-octadien-3-ol; 2,6-dimethyl-7-octen-2-ol; (α,α-4-trimethyl-3-cyclohexenyl)methanol; cis 3-hexen-1-ol; 9-decen-1-ol; and mixtures thereof.

6. A composition according to claim 1 further comprising from 0.01% to 0.05% chlorhexidine.

7. A composition according to claim 1 further comprising one or more adjunct ingredients, said adjunct ingredients are selected from the group consisting of:
  i) from 0.01% to about 3% by weight, of a low molecular weight polyol;
  ii) from 0.001% to about 0.3% by weight, of an aminocarboxylate chelator;
  iii) from 0.001% to about 5% by weight, of a copper salt, a zinc salt, or mixtures thereof;
  iv) from 0.001% to about 0.5% by weight, of a perfume;
  v) from 0.0001% to about 0.5% by weight, of an antimicrobial preservative; and
  vi) mixtures thereof.

8. A malodor control composition comprising:
  a) of a β-ketoester having the formula:

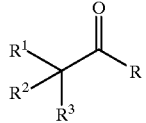

wherein R is alkoxy derived from a fragrance raw material alcohol selected from the group consisting of 3,7-dimethyl-1,6-octadien-3-ol; 2,6-dimethyl-7-octen-2-ol; (α,α-4-trimethyl-3-cyclohexenyl)methanol; cis 3-hexen-1-ol; 9-decen-1-ol; and mixtures thereof; $R^1$ has the formula:

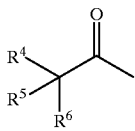

$R^2$ and $R^3$ are each hydrogen, $R^4$, $R^5$ and $R^6$ are taken together to form $C_6$–$C_{30}$ substituted or unsubstituted phenyl, naphthyl, and mixtures thereof;

b) from about 0.01% to about 5% by weight, of an uncomplexed cyclodextrin selected from the group consisting of α-cyclodextrin, hydroxypropyl-α-cyclodextrin, hydroxypropyl-β-cyclodextrin, methylated α-cyclodextrin, methylated β-cyclodextrin, and mixtures thereof; and c) the balance carriers and adjunct ingredients, said adjunct ingredients selected from the group consisting of:
   i) from 0.01% to about 3% by weight, of a low molecular weight polyol;
   ii) from 0.001% to about 0.3% by weight, of an aminocarboxylate chelator;
   iii) from 0.001% to about 5% by weight, of a copper salt, a zinc salt, or mixtures thereof;
   iv) from 0.001% to about 0.5% by weight, of a perfume;
   v) from 0.0001% to about 0.5% by weight, of an antimicrobial preservative; and
   vi) mixtures thereof.

9. A composition according to claim 8 further comprising from about 0.05% to about 0.3% by weight, of a surfactant selected from the group consisting of block copolymers of ethylene oxide and propylene oxide, polyalkyleneoxide polysiloxanes, alkyldiphenyl oxide disulfonate anionic surfactants having the formula:

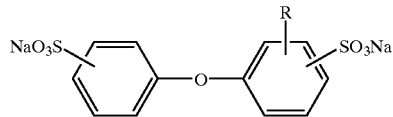

wherein R is $C_{12}$–$C_{22}$ linear or branched alkyl, and mixtures thereof.

* * * * *

UNITED STATES PATENT AND TRADEMARK OFFICE
CERTIFICATE OF CORRECTION

PATENT NO. : 6,100,233
DATED : August 8, 2000
INVENTOR(S) : Mark Robert Sivik et al.

It is certified that error appears in the above-identified patent and that said Letters Patent is hereby corrected as shown below:

Column 48, line 52, Claim 8, sub-paragraph a) should read -- a β-ketoester having the formula: -- . . .

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,100,233
DATED : August 8, 2000
INVENTOR(S) : Mark Robert Sivik et al.

It is certified that error appears in the above-identified patent and that said Letters Patent is hereby corrected as shown below:

<u>Column 48, claim 1</u>
Line 11, sub-paragraph b) should read -- from about 0.01% to about 5% by weight --.

Signed and Sealed this

Second Day of October, 2001

Attest:

*Nicholas P. Godici*

NICHOLAS P. GODICI
*Acting Director of the United States Patent and Trademark Office*

*Attesting Officer*